United States Patent [19]

Cronk et al.

[11] Patent Number: 4,870,975
[45] Date of Patent: Oct. 3, 1989

[54] SUCTION CANISTER ASSEMBLY FOR THE COLLECTION OF BODY FLUIDS AND TISSUE SPECIMENS

[76] Inventors: Scott Cronk, 8176 Shorewalk Dr., #D, Indianapolis, Ind. 46236; Michelle Thomas, 402 Tower Ct., Noblesville, Ind. 46060

[21] Appl. No.: 215,324

[22] Filed: Jul. 5, 1988

[51] Int. Cl.$^4$ .............................................. A61M 1/00
[52] U.S. Cl. .................................... 128/749; 128/760; 604/317; 604/319
[58] Field of Search ............................... 604/317–321; 128/740, 760–762

[56] References Cited

U.S. PATENT DOCUMENTS

| | | | |
|---|---|---|---|
| 3,768,478 | 10/1973 | Fertik et al. | 604/320 |
| 3,774,613 | 11/1973 | Woods, Jr. et al. | 128/304 |
| 3,929,133 | 12/1975 | Ragab | 604/119 |
| 4,111,204 | 9/1978 | Hessel | 604/321 |
| 4,195,633 | 4/1980 | Nehring et al. | 604/320 |
| 4,388,922 | 6/1983 | Telang | 604/319 |
| 4,443,220 | 4/1984 | Hauer et al. | 604/408 |
| 4,455,140 | 6/1984 | Joslin | 604/317 |
| 4,516,973 | 5/1985 | Telang | 604/319 |
| 4,522,623 | 6/1985 | Lauterjung | 604/319 |
| 4,643,197 | 2/1987 | Greene et al. | 128/762 |
| 4,675,010 | 6/1987 | Siposs et al. | 604/319 |

OTHER PUBLICATIONS

Brochure: Cabot Medical "Vacuum Curettage Systems and Accessories", 1988.
Cabot Medical "Introducing the Berkeley® Safe-Touch TM Collection System," 1989.

Primary Examiner—Dalton L. Truluck

[57] ABSTRACT

A suction canister assembly includes an outer collection bottle having a bottle mouth, an inner canister nested therein having a canister mouth and having a valve device at its bottom end, a dual closure lid closing off both the bottle mouth and the canister mouth and having an inlet port and an outlet port in communication with the canister, and a fluid porous specimen receptacle suspended from the lid and surrounding the inlet port. With the valve device open, a catheter assembly is exteriorly connected to the inlet port while negative pressure is applied to the outlet port. The catheter assembly is used for vacuum aspiration of a patient with solid material being retained within the receptacle and liquid material passes into the canister, through the valve device, and into the collection bottle. After completion of the procedure, the lid and inner canister combination may be removed from the collection bottle, the valve device closed and the solid material collected within the receptacle is safe for transport.

11 Claims, 1 Drawing Sheet

SUCTION CANISTER ASSEMBLY FOR THE COLLECTION OF BODY FLUIDS AND TISSUE SPECIMENS

FIELD OF THE INVENTION

The present invention relates to the field of suction canisters and more particularly to a suction canister assembly for the safe collection, transport and disposal of body fluids and tissue specimens from a patient.

BACKGROUND OF THE INVENTION

Vacuum aspiration has become popular in several surgical procedures including fat liposuctions, spontaneous miscarriages, and premeditated abortions. A typical apparatus used in abortion procedures is disclosed in U.S. Pat. No. 3,774,613 where an airtight collection bottle is connected to and in communication with a source of suction. One end of a suction catheter extends partially within the collection bottle. A filter trap surrounds the one end of the catheter within the bottle. With negative pressure maintained within the bottle, the distal end of the catheter is selectively positioned within the patient so that the negative pressure sucks the embryo, placenta and other matter from the uterine wall and evacuates such matter into filter trap within the collection bottle. Fluid material passes through the filter and is collected within the collection bottle while solid matter is retained in the filter trap.

Another vacuum aspiration device is disclosed in U.S. Pat. No. 3,929,133. There, a separate collection assembly is used with a water bottle and fluid reservoir to maintain separation between the liquid and solid material and to provide instantaneous visual examination as the operation proceeds. Other suction collection devices are disclosed in the following U.S. Patents:

| U.S. Pat. No. | Inventor |
| --- | --- |
| 4,675,010 | Siposs et al. |
| 4,643,197 | Greene et al. |
| 4,522,623 | Lauterjung |
| 4,516,973 | Telang |
| 4,455,140 | Joslin |
| 4,443,220 | Hauer et al. |
| 4,388,922 | Telang |
| 4,195,633 | Nehring et al. |
| 4,111,204 | Hessel |
| 3,768,478 | Fertik et al. |

With these and similar devices which filter solid matter from liquid matter, when the procedure is complete, the specimens contained in the filter trap (a mesh bag or stockinette) are prepared for transport to pathology for analysis. While still in the operating room, the specimens within the stockinette are separated from the liquid matter in the jar by removing the lid and withdrawing therewith the stockinette and its contents. It is frequently the case that the stockinette is so swollen with solid matter that it must literally be wrenched and twisted from the mouth of the bottle. In some cases, the stockinette must be cut and the contents withdrawn in sections. Once removed from the bottle, the specimens and stockinette, still dripping with blood, are placed on a tray or in another bottle and taken from the operating room to pathology for testing. The original collection bottle is emptied, taken by a scrub nurse from the operating room for cleaning and is then returned for another procedure. In many cases, the collection bottle is not sterilized, which enhances the possibility of contaminating the specimens of the subsequent procedure which can result in erroneous test results and misdiagnosis. The numerous instances of exposure to the air, the additional containers and the health technician also increase the chances of contaminating the specimen.

The risk to the various health care workers of contracting various diseases such as AIDS and hepatitis through contact with the stockinette and specimens and with the contaminated collection bottle is also great. The process of preparing the specimens for pathology, including having to wrench or cut a bloated specimen bag from the collection bottle, often results in blood splattering on and around the health care technician. Further, as a doctor, nurse or other health care technician leaves the operating room, his or her gloves must be removed and placed in a proper disposal container. This further enhances the risk of the technician's direct contact with the contaminated specimens or blood. In short, each additional transport and manipulation step which is required in association with the exposed and blood-soaked specimens, as well as with the dumping and cleaning of the collection bottle, poses a higher risk of exposure to disease to the technician. Further, the process of preparing the specimens for pathology including the removal and manipulation of the specimen bag from the bottle requires the consumption of valuable operating room time from one or more nurses or health technicians.

What is needed is a device which collects the solid material separately from the liquid material in a vacuum aspiration procedure and which allows for the more efficient and safe removal and transport of the solid material.

SUMMARY OF THE INVENTION

Generally speaking, a suction canister assembly is connectable to a vacuum source and collects body fluids and tissue specimens from a patient. The tissue specimens are quickly, easily and safely separable from the body fluids immediately after the procedure.

The above described suction canister assembly generally includes an outer collection bottle, an inner canister nested therein, a dual closure lid adapted to close off the top of both the collection bottle and the canister and a fluid-porous specimen receptacle nested within the canister for receiving through the lid body fluids and tissue specimens. The lid has an outlet port in communication with the canister and which is connectable to a source of suction to provide a partial vacuum within the canister. The lid also has an inlet port in communication with the canister and for receiving therethrough body fluids and tissue specimens. The specimen receptacle is a mesh stockinette which is suspended from the lid and surround the inlet port and into which the body fluids and tissue specimens flow. The canister has a valve device at its bottom which may be moved between an open and closed position. During a vacuum aspiration procedure, the valve device is in the open position, thereby permitting body fluids to pass through the inlet port, through the stockinette, into the canister, through the valve device and into the bottom of the collection bottle. Solid matter or tissue specimens are retained in the stockinette. After completion of the aspiration procedure, the lid is detached from the collection bottle and lifted away therefrom with the canister and stockinette still attached. The valve device at the bottom of the canister is moved to the closed position, thereby cutting off the flow of any residual body fluids from the canister. The lid, canister and tissue specimens may then be safely transported to pathology while the collection bottle may be emptied and cleaned for a subsequent procedure.

In another embodiment, the entire suction canister assembly is disposable and includes a plastic outer collection bottle and a disposal lid which covers and seals the outer bottle after the procedure is complete. The sealed outer bottle, with contents, may then be disposed appropriately as a unit.

It is an object of the present invention to provide an improved suction canister assembly for use in vacuum aspiration procedures.

It is another object of the present invention to provide a suction canister assembly which reduces the risk of contamination to the specimens collected.

It is another object of the present invention to provide a suction canister assembly which reduces the risk of contamination to specimens in subsequent procedures.

It is still another object of the present invention to provide a suction canister assembly which reduces the risk of exposure of the health worker while performing the various duties associated with the canister assembly.

Further objects and advantages of the present invention will become apparent from the following description of the preferred embodiment.

DESCRIPTION OF THE PREFERRED EMBODIMENT

Figure 1:
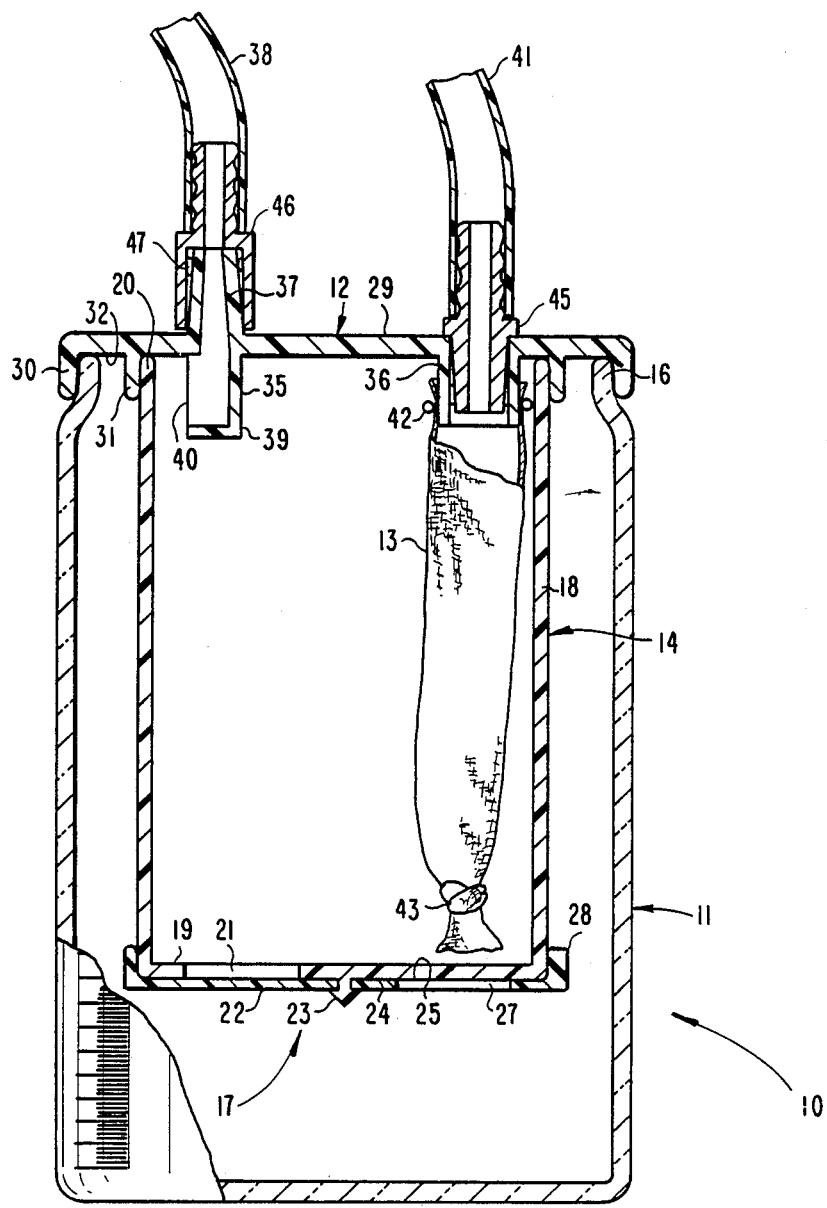
FIG. 1 is a side, partially cross-sectional view of a suction canister assembly in accordance with the preferred embodiment of the present invention.

For purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is shown a suction canister assembly 10 in accordance with the preferred embodiment of the present invention. Generally, suction canister assembly 10 includes outer collection bottle 11, dual closure lid 12, an inner canister 14 and a specimen receptacle or stockinette 13. Collection bottle 11 is a standard glass collection bottle and is generally cylindrical having a bottom and side walls and defining an upper open end or bottle mouth 16 which is exteriorly threaded to receive lid 12 thereupon. Inner canister 14 is also generally cylindrical having side walls 18, a bottom 19 and top open end or canister mouth 20 which is also exteriorly threaded to receive lid 12 thereupon. As shown in FIG. 1, the diameter of inner canister 14 is slightly less than the diameter of collection bottle 11 so that inner canister 14 can easily nest within collection bottle 11. Valve means 17 are provided at the bottom of inner canister 14 and include a hole 21 defined in bottom 19 and a plate 22. Plate 22 is pivotally mounted to bottom 19 by an appropriate pin 23. Pin 23 is an integral part of canister 14 with plate 22 having a central hole adapted to receive pin 23. Plate 22 is thereby tightly snapped onto and rotatably held by pin 23. One or more ears 28 are provided at the perimeter of plate 22 to facilitate turning plate 22 relative to canister 14. A complimentary hole 27 is defined in plate 22 and is alignable with hole 21 of bottom 19 at the proper angle of rotation of plate 22 about pin 23. Downwardly facing surface 24 of bottom 19 and upwardly facing surface 25 of plate 22 are formed in such a complimentary manner, and pin 23 holds plate 22 sufficiently tightly against bottom 19, that plate 22 will completely restrict flow through hole 21 whenever holes 21 and 27 are in no way aligned. Alternative valve means may also be provided in or near bottom 19 to shut off the flow of fluid from canister 14. The alternative valve means should, however, be easily operably, inexpensive, and unobtrusive to the operation of the rest of the canister assembly 10.

Lid 12 is unitary, injection-molded piece generally including a substantially flat top portion 29, a downwardly extending, outer circumferential flange portion 30, a downwardly extending, inner circumferential flange portion 31, an outlet port 35 and an inlet port 36. Both outer and inner circumferential flanges 30 and 31 are interiorly threaded for threaded engagement with collection bottle 11 and inner canister 14, respectively. A standard, annular paper gasket 32 is provided to provide an airtight seal between collection bottle 11 and lid 12. Seals of other types, such as o-rings may be used with lid 12 and collection bottle 11 being provided with the appropriate sealing surfaces.

Inlet port 36 is a generally cylindrical flange which extends downwardly from lid 12 and into canister 14 when the latter is secured to lid 12. Inlet port 36 is adapted to receive therethrough body fluids and tissue specimens from a patient through appropriate catheter means such as flexible tubing 41. Tubing 41 is secured in fluid-tight relation with lid 12, and specifically inlet port 36, by a standard male hose fitting 45. Within canister 14, a fluid porous specimen receptacle or stockinette 13 is secured to inlet port 36 in any desired manner, as by elastic ring 42. Stockinette 13 is a length of standard gauze or mesh tubing which has been tied off at one end 43. Inlet port 35 is a generally cylindrical flange which extends both above and below lid 12. The upper portion 37 of inlet port 35 is connected to an appropriate source of suction as by a female hose fitting 46, o-ring 47 and flexible tubing 38. In order to keep stockinette 13 from being sucked up against and blocking the opening in outlet port 35, lower portion 39 is provided with a side opening 40 which faces away from inlet port 36 and stockinette 13 connected thereto.

When a procedure such as a spontaneous miscarriage, premeditated abortion or fat liposuction is to be performed, a suction canister assembly 10 is assembled as shown in FIG. 1, except with plate 22 rotated so that holes 21 and 27 are aligned. Tubing 38 is connected with a source of suction. As is well known in the art, an overflow bottle may be connected serially between tubing 38 and the source of suction. An appropriate catheter or vacuum curette (not shown) is connected to the distal end of tubing 41 for insertion into the patient and for application of negative pressure to the affected area of the patient. The source of suction is activated creating negative pressure or a partial vacuum through tubing 38, outlet port 35, canister 14, inlet port 36 and tubing 41. Matter sucked from the affected area of the patient will pass through tubing 41, through inlet port 36 and into stockinette 13 where the majority of solid matter is retained while fluid matter passes through the mesh of stockinette, into canister 14 and down through aligned holes 21 and 27. As the procedure continues, stockinette 13 will swell to accommodate the increasing volume of solid material retained therein. If the fluid level increases to and above the bottom of lower portion 39 of outlet port 35, fluid matter will be sucked through outlet port 35, through tube 38 and into the overflow bottle described above.

After completion of the procedure, the source of suction is deactivated and tubing 41 is detached from lid 12 and discarded. As tubing 38 (leading to the source of suction, with or without an overflow bottle connected therebetween) is downstream of the specimen in reference to the vacuum path, there is little chance of contamination to future procedures. It is therefore usually detached from lid 12, cleaned and used again. Lid 12 is unscrewed from collection bottle 11. Lid 12, with canister 14 still attached, is lifted upwardly and held above bottle 11 until the majority of liquid material has flowed through openings 21 and 27. Plate 22 is then manually rotated to close valve means 17 and stop the flow of fluid material from within canister 14. The health technician may then wipe off any excess material on the outside of canister 14. To this point, the chances of the health technician's direct contact with fluid material of the tissue specimen due to splattering has been greatly reduced. The technician is still guarded for the most part from direct contact by the operating room gown and gloves. The tissue specimens within stockinette 13 have likewise had no substantial contaminating contact with the exterior. Canister 14, lid 12, stockinette 13 and the specimens located therein may now be more safely transported to pathology for analysis by a health technician who has discarded the operating room gloves. The contents of collection bottle 11 are appropriately discarded and bottle 11 is cleaned for another procedure. Although stockinette 13 may have become so bloated with solid material that it substantially fills canister 14 making it difficult to remove the specimens from the canister, the operating room technician will not have to come in contact with the contents of the canister. Instead, canister 14, with specimens therein, will be transported to pathology where the attending technicians, who will have to manipulate the specimens anyway, will perform the process of removing the specimens and stockinette 13 from canister 14. Also, although the cleaning process of collection bottle 11 may not include sterilization, the present invention reduces the risk of contamination to the tissue specimens within stockinette 13 because stockinette 13 cannot come in contact with the walls of collection bottle 11. Lid 12 and canister 14 are both made of a disposable plastic permitting them to be discarded in accordance with standard hospital procedures.

Alternative embodiments are contemplated for a completely disposable suction canister assembly. Such an embodiment would include collection bottle 11 being made of a plastic such as polyvinylchloride with sufficient strength to withstand negative pressures of the suction procedure. After completion of the aspiration procedure, and removal of the canister lid and stockinette, an appropriate disposal lid is tightly screwed to the top of the disposable collection bottle, and the combination disposable bottle and lid with fluid material therein may then be appropriately discarded as a unit. Such a disposal lid (not shown) would be a standard know jar lid, similar to lid 12 but without the inlet or outlet ports, without an inner flange portion 31, and adapted only to seal shut bottle mouth 16.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A suction canister assembly for the collection of body fluids and tissue specimens from a patient, comprising:
   an outer collection bottle having a bottle mouth;
   an inner canister nested within said bottle and having a canister mouth and a bottom end and having valve means for selectively permitting the passage of material out of said canister;
   a dual closure lid openably closing both the bottle mouth and the canister mouth, said lid having an outlet port adapted for connection with a source of suction and an inlet port for receiving therethrough body fluids and tissue specimens from a patient, both the inlet port and the outlet port opening into said canister; and,
   a fluid porous specimen receptacle suspended from said lid and within said canister and disposed about said inlet port so as to filter any material entering said canister through said inlet port.

2. The suction canister assembly of claim 1 wherein the valve means includes an opening in the bottom end and closure means connected to said canister for selectively closing said opening.

3. The suction canister assembly of claim 2 wherein said closure means is a plate rotatably mounted to the bottom end, the plate having a hole alignable with the opening by rotating the plate relative to said canister.

4. The suction canister assembly of claim 1 wherein said dual closure lid includes:
   a top portion,
   a downwardly extending, outer circumferential flange portion for engagement with said bottle, and
   a downwardly extending, inner circumferential flange portion for engagement with said canister.

5. The suction canister assembly of claim 4 further including a gasket for providing an air-tight seal between said bottle and said lid, said gasket disposed between the inner and outer flange portions.

6. The suction canister assembly of claim 1 wherein said lid and said canister are disposable.

7. A method for collecting body fluids and tissue specimens from a patient, comprising the steps of:
   providing a dual closure lid having an outlet port and an inlet port;
   connecting a fluid porous specimen receptacle to said lid and surrounding the inlet port so as to filter any material passing through the inlet port;
   providing an inner canister having a canister mouth and a bottom end opposite the mouth, the bottom end having valve means for selectively permitting passage of material out of the bottom end of said canister;
   removably securing said lid to said canister so that said lid covers the mouth with the receptacle resting within said canister
   opening the valve means;
   providing a collection bottle having a bottle mouth;

removably securing said lid to said collection bottle so that said lid sealingly covers the bottle mouth with said canister nested within said collection bottle;

providing catheter means for providing a conduit for body fluids and tissue specimens from the patient to the inlet port;

connecting the catheter means to the inlet port;

applying a negative pressure through the outlet port and to said bottle; and, maneuvering the distal end of the catheter means adjacent the body fluids and tissue specimens of the patient which are to be collected.

8. The method for collecting body fluids and tissue specimens from a patient of claim 7 further including the steps of:

after completing the maneuvering step, disengaging the negative pressure from said bottle and detaching the catheter means from the inlet port;

detaching said lid from said bottle and lifting said lid and canister from said bottle; and, closing the valve means.

9. The method for collecting body fluids and tissue specimens from a patient of claim 7 wherein said providing an inner canister step includes the valve means including an opening in the bottom end of said canister and a plate rotatably mounted to the bottom end, the plate having a hole alignable with the opening by rotating the plate relative to said canister.

10. The method for collecting body fluids and tissue specimens from a patient of claim 7 wherein said providing a dual closure lid step includes said lid having a top portion, a downwardly extending, outwardly circumferential flange portion for engagement with said bottle, and a downwardly extending, inner circumferential flange portion for engagement with said canister.

11. The method for collecting body fluids and tissue specimens from a patient of claim 10 wherein said providing a dual closure lid step includes said lid being disposal and wherein said providing an inner canister step includes said canister being disposable.

* * * * *